(12) United States Patent
Kim

(10) Patent No.: US 8,932,057 B2
(45) Date of Patent: *Jan. 13, 2015

(54) DENTAL FILING TOOL HANDLE

(71) Applicant: Daniel Sung-Yul Kim, Vancouver, WA (US)

(72) Inventor: Daniel Sung-Yul Kim, Vancouver, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/048,695

(22) Filed: Oct. 8, 2013

(65) Prior Publication Data

US 2014/0038131 A1  Feb. 6, 2014

Related U.S. Application Data

(63) Continuation-in-part of application No. 13/715,733, filed on Dec. 14, 2012, now Pat. No. 8,602,778.

(60) Provisional application No. 61/639,804, filed on Apr. 27, 2012.

(51) Int. Cl.
*A61C 3/06* (2006.01)
*A61C 5/12* (2006.01)

(52) U.S. Cl.
CPC .. *A61C 3/06* (2013.01); *A61C 5/125* (2013.01)
USPC ........................................................ 433/142

(58) Field of Classification Search
USPC .................. 433/141–144, 146, 147
See application file for complete search history.

(56) References Cited

U.S. PATENT DOCUMENTS

| | | | |
|---|---|---|---|
| 2,288,011 A | 6/1942 | Mizzy | |
| D576,730 S | 9/2008 | Kim | |
| 7,455,521 B2 | 11/2008 | Fishburne, Jr. | |
| D600,810 S | 9/2009 | Khouri | |
| 7,824,182 B2 | 11/2010 | Kim | |
| 7,914,284 B2 | 3/2011 | Kim | |
| D638,127 S | 5/2011 | Khouri | |
| 8,535,057 B2 | 9/2013 | Kim | |
| 8,602,778 B2 * | 12/2013 | Kim | 433/142 |
| 2005/0271999 A1 | 12/2005 | Fishburne | |
| 2006/0063131 A1 | 3/2006 | Kim | |
| 2006/0127845 A1 | 6/2006 | Khouri | |
| 2006/0183075 A1 | 8/2006 | Kim | |
| 2012/0258425 A1 * | 10/2012 | Rek | 433/142 |
| 2014/0038131 A1 | 2/2014 | Kim | |

* cited by examiner

*Primary Examiner* — Heidi M Eide
*Assistant Examiner* — Matthew Saunders
(74) *Attorney, Agent, or Firm* — Mark E. Beatty; Kurt M. Rylander; Rylander & Assoc. PC

(57) ABSTRACT

An improved handle for a dental filing tool, the tool having an arcuate handle with a horizontal bridge and opposed first and second vertical arms, the improvement including first and second sets of partial-cylindrical grip portions distributed along the outer surfaces of the first and second vertical arms, respectively, the grip portions aligned normal to the handle plane, the respective first and second sets defining convex or concave outer grip profiles and concave front-back grip profiles. An improved handle may further include an embedded socket to receive a coupler for a dental driver, or a projecting coupling to engage a dental driver coupling.

30 Claims, 12 Drawing Sheets

DENTAL FILING TOOL HANDLE

CROSS-REFERENCE TO RELATED APPLICATIONS

This application is a continuation-in-part of, and claims priority to, co-pending U.S. patent application Ser. No. 13/715,733, filed Dec. 14, 2012, which is a nonprovisional application of, and claims priority to, U.S. Provisional Application Ser. No. 61/639,804, filed Apr. 27, 2012, the disclosures of each of which are hereby incorporated by reference.

FIELD OF THE INVENTION

The present invention relates to dental filing tools. More particularly, the present invention relates to improved dental filing tools usable by manual manipulation or mountable to a motorized dental driver.

BACKGROUND

The current conventional method for fitting dental crowns, bridges, onlays and inlays, herein referred to generally as restorations, involves the dental practitioner sliding colored carbon paper, of which the thickness is the recommended measured distance between teeth, between the interproximal area of the tooth and the restoration. The carbon paper marks with carbon ink the proximal contact area where the two surfaces of the teeth and/or restoration are too dose, and then the practitioner grinds the restoration with a rotary instrument to remove excess material.

Another method employed is the stand alone use of a metal filing strip coated with some superfine abrasive material. The metal filing strip is inserted into the interproximal area to file down the proximal contact area of the crown for an accurate fit. Since the space between the tooth and the crown, bridge, onlay, and inlay must not be too close or too spaced apart the practitioner must file incrementally. These steps are repeated until the desired distance between the tooth and the restoration is achieved. Because the filing strip is extremely thin, narrow, and malleable, it is necessary for the practitioner to maintain tension in the strip by holding it taunt at opposite ends with fingers from both hands. Unfortunately holding the filing strip in such as manner is cumbersome in the patient's mouth and impedes the practitioner from achieving desired angles and restricts range of motion to effectively file. Especially when the patient is receiving crowns, bridges, onlays, or inlays in the back of the mouth where it is considerably more difficult to access, it is difficult for the practitioner to file since both hands are needed to hold tension in the strip and often a patient's mouth is too small or cannot open wide enough to accommodate the file comfortably. As a result, the patient must endure strenuous stretching of the lips and jaw area. Often a practitioner struggles to find the best placement for fingers to pinch the strip to create sufficient tension while attempting to minimize the restricting presence of both hands in the patient's mouth. This method is inefficient, tiresome for the practitioner, and uncomfortable for the patient. Moreover, because of the difficulty involved handling the filing strip, often patients sustain suffer small cuts due to the sharp edges of the strip coming in contact with gums and lips while filing the tooth or restoration.

Another method employed is that a thin metal strip coated with fine abrasive material is fastened to a removable bow which is attached an extending handle. Generally, the bow and handle are too long to maneuver in the mouth and limit the size of abrasive strip which is actually providing a working surface, such that it is ineffective for posterior teeth. Additionally, it is difficult to grip the device by the protruding handle, and the protruding handle interferes with gripping from the ends. These drawbacks have been addressed by tools manufactured as unitary handles with the filing strip ends embedded within the arms, or by provided improved positive capture methods for the strips, such as by clamping within the arms—through apertures in the strip ends—using snap fittings.

Generally, hand-held filing apparatus are useful, but can rapidly cause fatigue for the user due to difficulties gripping the device. Purely rectilinear arrangements create flat, smooth opposed surfaces which allow for only one orientation of the gripping fingers—i.e. horizontal. Additionally, sharp corners at the joints inhibit diagonal grips. Front-back gripping is possible, but is still less effective than that provided by a shaped surface. Additionally, knurled surfaces, or surfaces with uniform dispersions of small protrusions or indents, are not particularly effective to enhance gripping on such a small device, especially within the wet and slimy environment of a patient's mouth. These limitations may apply regardless whether the tool is of assembled or unitary construction, and regardless whether the strip is held in tension or bowed.

The present invention solves these problems by providing an improved handle disposed along the outer surfaces of a tool handle, which is compatible with unitary or assembled tools, and which is compatible with filing tools which can be used manually or coupled to a dental driver mechanism.

SUMMARY AND ADVANTAGES

The improved handle of the present invention presents numerous advantages, including: (1) provides improved grip with improved orientation to prevent slippage; (2) the use of partial-cylindrical gripping portions provides positive separation to allow saliva to run off between the grip portions rather than accumulating, a common problem in dimpled or cross-hatched grips; (3) is useful for both manual files, and for manual files couplable to a power driven dental driver tool; (4) is useful for unitary handles with a file strip formed into the handle, and for handles designed to be assembled on-site with a file strip; (5) is useful for handles which hold an abrasive strip under tension, as well as handles which hold an abrasive strip with a bow in the strip; (6) is amenable to injection molding methods.

Additional advantages of the invention will be set forth in part in the description which follows, and in part will be obvious from the description, or may be learned by practice of the invention. The advantages of the invention may be realized and attained by means of the instrumentalities and combinations particularly pointed out in the appended claims. Further benefits and advantages of the embodiments of the invention will become apparent from consideration of the following detailed description given with reference to the accompanying drawings, which specify and show preferred embodiments of the present invention.

BRIEF DESCRIPTION OF THE DRAWINGS

The accompanying drawings, which are incorporated into and constitute a part of this specification, illustrate one or more embodiments of the present invention and, together with the detailed description, serve to explain the principles and implementations of the invention.

REFERENCE NUMBERS USED IN DRAWINGS

Figure 1:
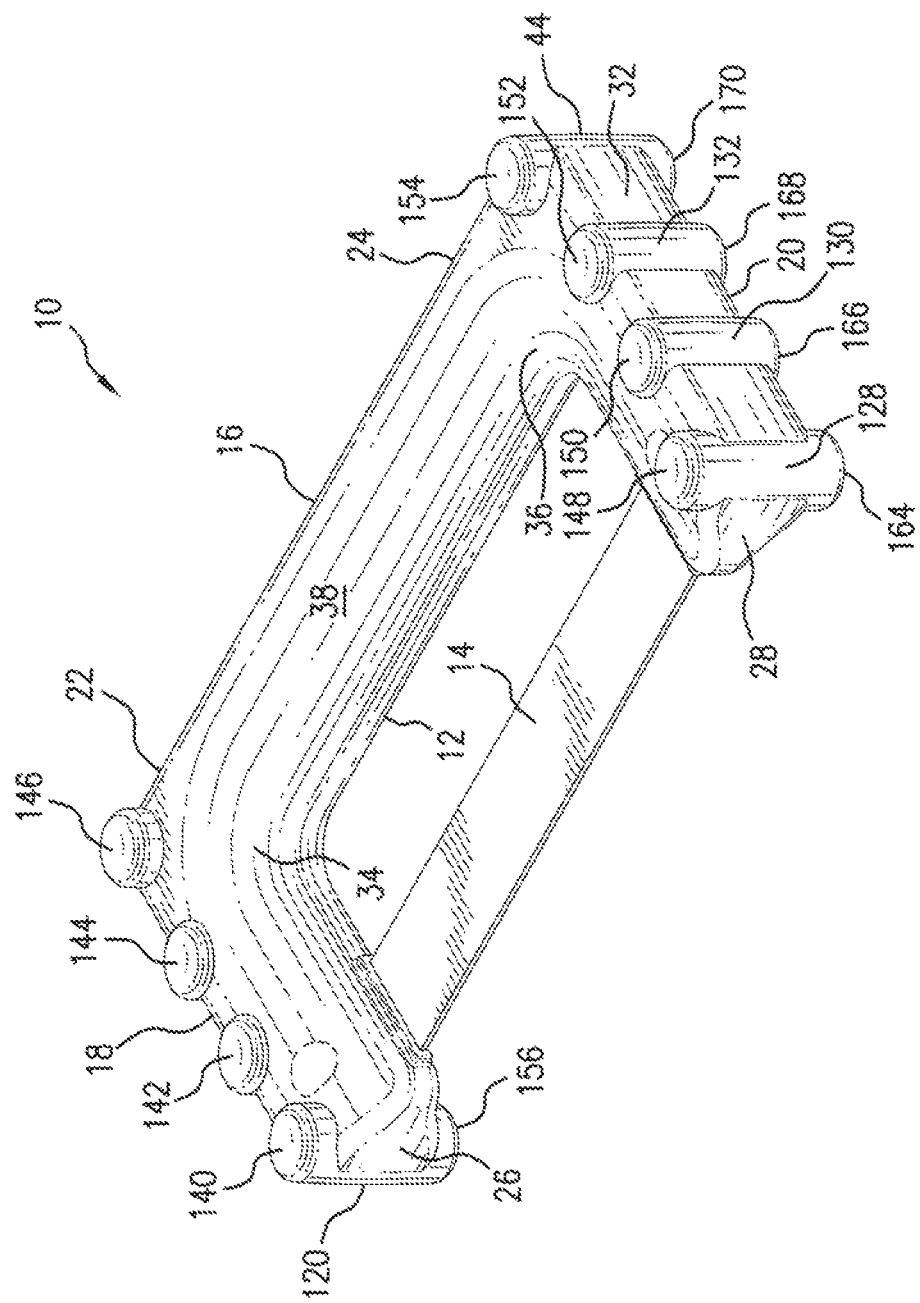
FIG. 1 shows a perspective view of a first embodiment.

Turning now descriptively to the drawings, in which similar reference characters denote similar elements throughout the several views, the figures illustrate the present invention. With regard to the reference numerals used, the following numbering is used throughout the various drawing figures:

10 First Embodiment
12 Handle
14 Filing Strip
16 Horizontal Bridge
18 First Vertical Arm
20 Second Vertical Arm
22 First Horizontal Bridge End
24 Second Horizontal Bridge End
26 First Vertical Arm Terminal End
28 Second Vertical Arm Terminal End
30 First Vertical Arm Outer Surface
32 Second Vertical Arm Outer Surface
34 First Vertical Arm—Horizontal Bridge Connection Region
36 Second Vertical Arm—Horizontal Bridge Connection Region
38 Handle Front Surface
40 Handle Back Surface
42 Handle Corner/Connection Region of First Vertical Arm
44 Handle Corner/Connection Region of Second Vertical Arm
46 Bridge Outer Surface
100 First Set of Grip Portions
102 Second Set of Grip Portions
104 First Grip Portion on First Vertical Arm
106 Interstitial Grip Portion on First Vertical Arm
108 Interstitial Grip Portion on First Vertical Arm
110 Second Grip Portion on First Vertical Arm
112 First Grip Portion on Second Vertical Arm
114 Interstitial Grip Portion on Second Vertical Arm
116 Interstitial Grip Portion on Second Vertical Arm
118 Second Grip Portion on Second Vertical Arm
120 Outer surface of First Grip Portion on First Vertical Arm
122 Outer surface of Interstitial Grip Portion on First Vertical Arm
124 Outer surface of Interstitial Grip Portion on First Vertical Arm
126 Outer surface of Second Grip Portion on First Vertical Arm
128 Outer surface of First Grip Portion on Second Vertical Arm
130 Outer surface of Interstitial Grip Portion on Second Vertical Arm
132 Outer surface of Interstitial Grip Portion on Second Vertical Arm
134 Outer surface of Second Grip Portion on Second Vertical Arm
136 First Convex Grip Profile
138 Second Convex Grip Profile
140 First End Surface of First Grip Portion on First Vertical Arm
142 First End Surface of Interstitial Grip Portion on First Vertical Arm
144 First End Surface of Interstitial Grip Portion on First Vertical Arm
146 First End Surface of Second Grip Portion on First Vertical Arm
148 First End Surface of First Grip Portion on Second Vertical Arm
150 First End Surface of Interstitial Grip Portion on Second Vertical Arm
152 First End Surface of Interstitial Grip Portion on Second Vertical Arm
154 First End Surface of Second Grip Portion on Second Vertical Arm
156 Second End Surface of First Grip Portion on First Vertical Arm
158 Second End Surface of Interstitial Grip Portion on First Vertical Arm
160 Second End Surface of interstitial Grip Portion on First Vertical Arm
162 Second End Surface of Second Grip Portion on First Vertical Arm
164 Second End Surface of First Grip Portion on Second Vertical Arm
166 Second End Surface of Interstitial Grip Portion on Second Vertical Arm
168 Second End Surface of Interstitial Grip Portion on Second Vertical Arm
170 Second End Surface of Second Grip Portion on Second Vertical Arm
172 First Vertical Arm Front Concave Grip Profile
174 Second Vertical Arm Front Concave Grip Profile
176 First Vertical Arm Back Concave Grip Profile
178 Second Vertical Arm Back Concave Grip Profile
1010 Second Embodiment
1012 Handle
1014 Filing Strip
1016 Horizontal Bridge
1018 First Vertical Arm
1020 Second Vertical Arm
1022 First Horizontal Bridge End
1024 Second Horizontal Bridge End
1026 First Vertical Arm Terminal End
1028 Second Vertical Arm Terminal End
1030 First Vertical Arm Outer Surface
1032 Second Vertical Arm Outer Surface
1034 First Vertical Arm—Horizontal Bridge Connection Region
1036 Second Vertical Arm—Horizontal Bridge Connection Region
1038 Handle Front Surface
1040 Handle Back Surface
1042 Handle Corner/Connection Region of First Vertical Arm
1044 Handle Corner/Connection Region of Second Vertical Arm
1046 Bridge Outer Surface 1048 Receiving Socket
1050 Coupler
1052 Dental Driver
1100 First Set of Grip Portions
1102 Second Set of Grip Portions
1104 First Grip Portion on First Vertical Arm
1106 Interstitial Grip Portion on First Vertical Arm
1108 Interstitial Grip Portion on First Vertical Arm
1110 Second Grip Portion on First Vertical Arm
1112 First Grip Portion on Second Vertical Arm
1114 Interstitial Grip Portion on Second Vertical Arm
1116 Interstitial Grip Portion on Second Vertical Arm
1118 Second Grip Portion on Second Vertical Arm
1120 Outer surface of First Grip Portion on First Vertical Arm
1122 Outer surface of interstitial Grip Portion on First Vertical Arm
1124 Outer surface of Interstitial Grip Portion on First Vertical Arm
1126 Outer surface of Second Grip Portion on First Vertical Arm
1128 Outer surface of First Grip Portion on Second Vertical Arm
1130 Outer surface of Interstitial Grip Portion on Second Vertical Arm
1132 Outer surface of Interstitial Grip Portion on Second Vertical Arm
1134 Outer surface of Second Grip Portion on Second Vertical Arm
1136 First Convex Grip Profile
1138 Second Convex Grip Profile
1140 First End Surface of First Grip Portion on First Vertical Arm
1142 First End Surface of Interstitial Grip Portion on First Vertical Arm
1144 First End Surface of Interstitial Grip Portion on First Vertical Arm
1146 First End Surface of Second Grip Portion on First Vertical Arm
1148 First End Surface of First Grip Portion on Second Vertical Arm
1150 First End Surface of Interstitial Grip Portion on Second Vertical Arm
1152 First End Surface of Interstitial Grip Portion on Second Vertical Arm
1154 First End Surface of Second Grip Portion on Second Vertical Arm
1156 Second End Surface of First Grip Portion on First Vertical Arm
1158 Second End Surface of Interstitial Grip Portion on First Vertical Arm
1160 Second End Surface of Interstitial Grip Portion on First Vertical Arm
1162 Second End Surface of Second Grip Portion on First Vertical Arm
1164 Second End Surface of First Grip Portion on Second Vertical Arm
1166 Second End Surface of Interstitial Grip Portion on Second Vertical Arm
1168 Second End Surface of Interstitial Grip Portion on Second Vertical Arm
1170 Second End Surface of Second Grip Portion on Second Vertical Arm
1172 First Vertical Arm Front Concave Grip Profile
1174 Second Vertical Arm Front Concave Grip Profile
1176 First Vertical Arm Back Concave Grip Profile
1178 Second Vertical Arm Back Concave Grip Profile
2010 Third Embodiment
2012 Handle
2014 Filing Strip
2016 Horizontal Bridge
2018 First Vertical Arm
2020 Second Vertical Arm
2022 First Horizontal Bridge End
2024 Second Horizontal Bridge End
2026 First Vertical Arm Terminal End
2028 Second Vertical Arm Terminal End
2030 First Vertical Arm Outer Surface
2032 Second Vertical Arm Outer Surface
2034 First Vertical Arm—Horizontal Bridge Connection Region
2036 Second Vertical Arm—Horizontal Bridge Connection Region
2038 Handle Front Surface
2040 Handle Back Surface
2042 Handle Corner/Connection Region of First Vertical Arm
2044 Handle Corner/Connection Region of Second Vertical Arm
2046 Bridge Outer Surface
2048 Projecting Coupler
2050 Dental Driver Tool Coupler
2052 Dental Driver
2100 First Set of Grip Portions
2102 Second Set of Grip Portions
2104 First Grip Portion on First Vertical Arm
2106 Interstitial Grip Portion on First Vertical Arm
2108 Interstitial Grip Portion on First Vertical Arm
2110 Second Grip Portion on First Vertical Arm
2112 First Grip Portion on Second Vertical Arm
2114 Interstitial Grip Portion on Second Vertical Arm
2116 Interstitial Grip Portion on Second Vertical Arm
2118 Second Grip Portion on Second Vertical Arm
2120 Outer surface of First Grip Portion on First Vertical Arm
2122 Outer surface of interstitial Grip Portion on First Vertical Arm
2124 Outer surface of Interstitial Grip Portion on First Vertical Arm
2126 Outer surface of Second Grip Portion on First Vertical Arm
2128 Outer surface of First Grip Portion on Second Vertical Arm
2130 Outer surface of Interstitial Grip Portion on Second Vertical Arm
2132 Outer surface of Interstitial Grip Portion on Second Vertical Arm
2134 Outer surface of Second Grip Portion on Second Vertical Arm
2136 First Concave Grip Profile
2138 Second Concave Grip Profile
2140 First End Surface of First Grip Portion on First Vertical Arm
2142 First End Surface of Interstitial Grip Portion on First Vertical Arm
2144 First End Surface of Interstitial Grip Portion on First Vertical Arm
2146 First End Surface of Second Grip Portion on First Vertical Arm
2148 First End Surface of First Grip Portion on Second Vertical Arm
2150 First End Surface of Interstitial Grip Portion on Second Vertical Arm 2152 First End Surface of Interstitial Grip Portion on Second Vertical Arm
2154 First End Surface of Second Grip Portion on Second Vertical Arm
2156 Second End Surface of First Grip Portion on First Vertical Arm
2158 Second End Surface of Interstitial Grip Portion on First Vertical Arm
2160 Second End Surface of Interstitial Grip Portion on First Vertical Arm
2162 Second End Surface of Second Grip Portion on First Vertical Arm
2164 Second End Surface of First Grip Portion on Second Vertical Arm
2166 Second End Surface of Interstitial Grip Portion on Second Vertical Arm
2168 Second End Surface of Interstitial Grip Portion on Second Vertical Arm
2170 Second End Surface of Second Grip Portion on Second Vertical Arm
2172 First Vertical Arm Front Concave Grip Profile
2174 Second Vertical Arm Front Concave Grip Profile
2176 First Vertical Arm Back Concave Grip Profile
2178 Second Vertical Arm Back Concave Grip Profile
2180 Projecting Coupler First Part
2182 Projecting Coupler Second Part
2184 Hollow Tube Coupling
2186 Tube Coupling First End
2188 Tube Coupling Second End
2190 Tube Coupling Open Seam
2192 Projecting Coupler/Filing Strip Overlap

DETAILED DESCRIPTION

Before beginning a detailed description of the subject invention, mention of the following is in order. When appropriate, like reference materials and characters are used to designate identical, corresponding, or similar components in differing figure drawings. The figure drawings associated with this disclosure typically are not drawn with dimensional accuracy to scale, i.e., such drawings have been drafted with a focus on clarity of viewing and understanding rather than dimensional accuracy.

In the interest of clarity, not all of the routine features of the implementations described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another. Moreover, it will be appreciated that such a development effort might be complex and time-consuming, but would nevertheless be a routine undertaking of engineering for those of ordinary skill in the art having the benefit of this disclosure.

Figure 2:
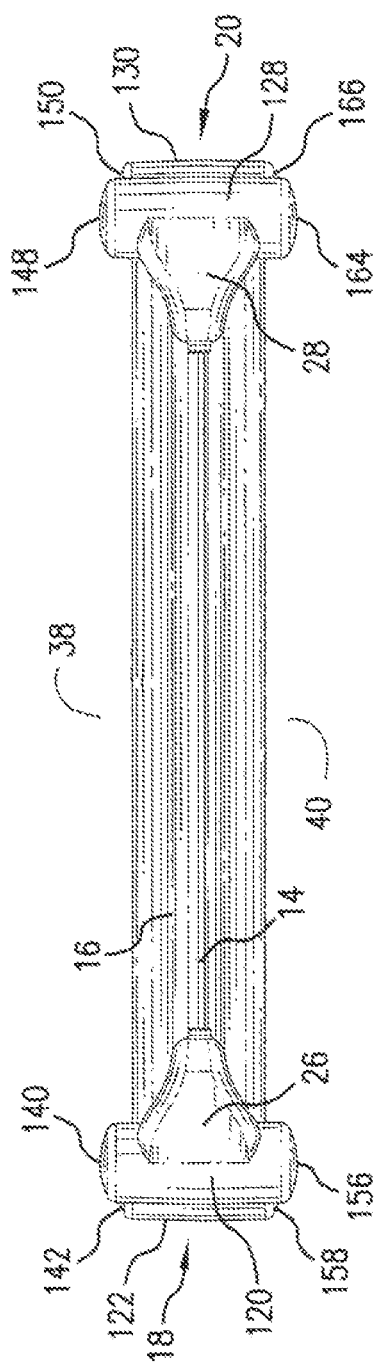
FIG. 2 shows bottom edge view of a first embodiment.
Figure 3:
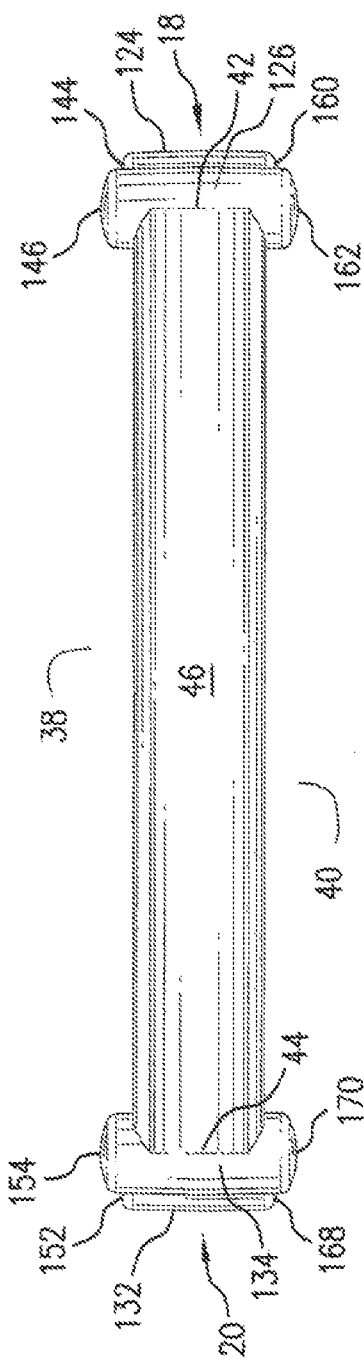
FIG. 3 shows a top edge view of a first embodiment.
Figure 4:
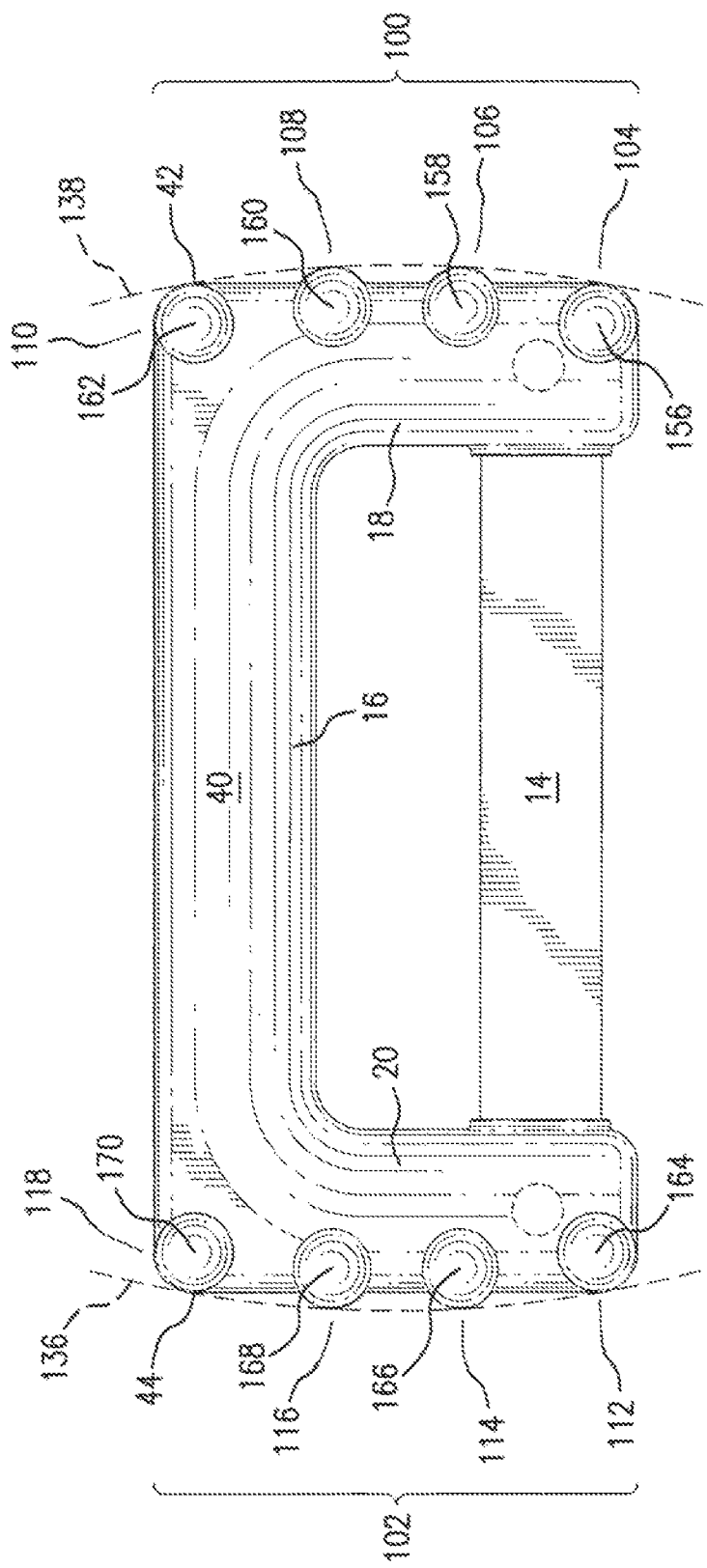
FIG. 4 shows back view of a first embodiment.
Figure 5:
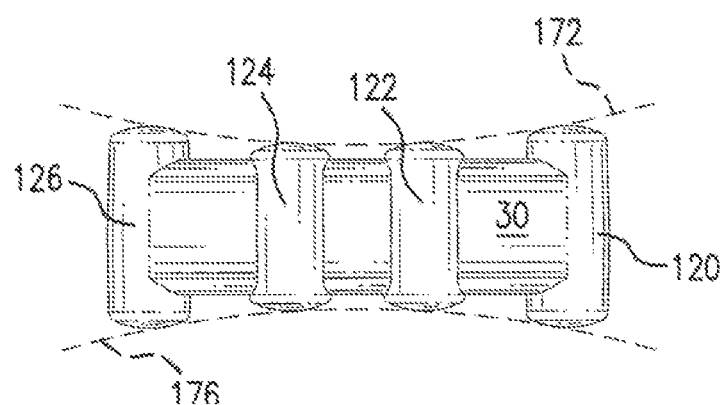
FIG. 5 shows side view of a first embodiment.
Figure 6:
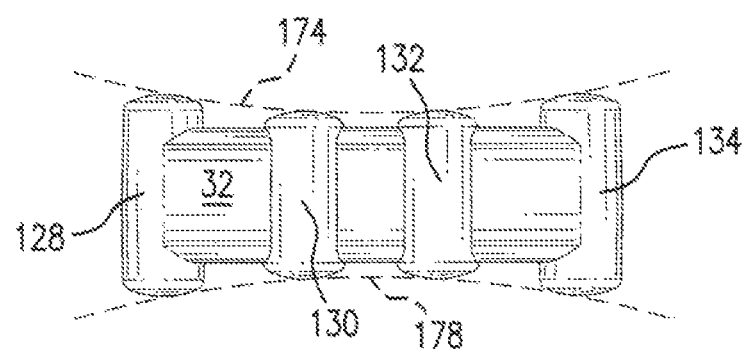
FIG. 6 shows side view of a first embodiment.

Referring to FIGS. 1-6, a first embodiment of an improved dental filing tool 10 is provided. FIGS. 1-6 generally demonstrate a pre-existing design. Referring to FIGS. 1-6, the pre-existing apparatus includes arcuate handle 12 and a filing strip 14. Handle 12 includes a horizontal bridge 16 and opposed first and second vertical arms 18, 20 extending in parallel from opposite ends 22, 24 of the bridge to terminal ends 26, 28, the vertical arms 18, 20 having outer surfaces 30, 32, respectively, and being adapted to hold filing strip 14 extending between them, the horizontal bridge 16 and vertical arms 18, 20 generally defining a handle plane.

The improvement includes first and second sets 100, 102 of partial-cylindrical grip portions 104, 106, 108, 110 and 112, 114, 116, 118, respectively, distributed along the outer surfaces 30, 32 of the first and second vertical arms 18, 20, respectively, the grip portions 104-118 extending longitudinally from a first end surface, 140-154, respectively, proximate to—and extending past—the handle front surface to a second end surface 156-170, respectively, proximate to—and extending past—the handle back surface. The partial-cylindrical grip portions 104-118 are aligned normal (i.e. with the longitudinal axis aligned transversely) to the handle plane. Grip portions 104-118 are described as "partial-cylindrical" because the general shape of the protruding portion of their profiles appears like a cylinder embedded transversely within the respective handle vertical arms 18 and 20. Rounded cross-sections such as circles or ovals may provide greater comfort, but a user may prefer sharper edges for use with thicker latex gloves. Rounded cross-sections also make it easier to apply a rounded end surface (140-170) if desired, because the three-dimensional shape is less complex. Additionally, rounded shapes may be easier to produce by injection molding methods, with less dimensional instability problems (common at corner profiles) and more uniform melting.

Each set 100, 102 includes a first grip portion 102, 112 disposed proximate the respective vertical arm terminal end 26, 28, a second grip portion 110, 118 disposed proximate the connection region 34, 36 of the bridge 16 and respective vertical arm 18, 20, and a plurality of spaced-apart interstitial grip portions 106, 108 and 114, 116 distributed between the first and second grip portions 104, 110 and 112, 118, respectively.

The outer surfaces 120, 122, 124, 126 and 128, 130, 132, 134 of each of the first and second sets 100, 102, respectively, trace a convex grip profile, 136, 138, respectively. Outer surfaces 120-134 refer to the exposed exterior surfaces proximate the first and second arm outer surfaces 30, 32, and excluding end surfaces 140-170. Convex grip profiles 136, 138, can be described as tangent arcs, as each represents a continuous arc intersecting a point on the perimeter or outer surface 120-134 of each grip portion 104-118.

Each grip portion 104-118 extends from a first end surface 140, 142, 144, 146, 148 150, 152, 154, respectively, to a second end surface 156, 158, 160, 162, 164, 166, 168, 170, respectively. The respective end surfaces 140-154 project outward from the respective front and back handle surfaces, 38 and 40, to provide enhanced grip when held front-back (in the embodiment, the handle front and back form mirror images). In the embodiment, the end surfaces of each of first and second sets 100, 102 of grip portions 104-118, project outward from the handle front and back surfaces 38, 40, and trace a concave grip profile 172, 174, 176, 178, with each of the first and second grip portions 104, 112 and 110,116, respectively, projecting farther than the respective interstitial grip portions 106, 108 and 114, 116. In the embodiment, the concave grip profiles 172-178 trace a tangent arc which intersects with the end-point of each end surface 140-146, 148-154, 156-162 and 164-170, respectively.

In the embodiment, each of the grip portion first and second end surfaces 140-170 are rounded, in this case semispherical. Other end surface profiles could be used as well. The rounded surfaces provide greater comfort when tightly gripped.

In the embodiment, each first grip portion 104, 112 is located at the vertical arm terminal end 24, 26, respectively. Each first grip portion 104, 112 radius matches the corner radius of its respective vertical arm terminal end, 24, 26 such that each outer surface 120, 128 of the respective first grip portion 104, 112 is flush with the outer surface of the vertical arm terminal end 26, 28, respectively.

In the embodiment, each of the second grip portions, 110 and 118, respectively, is located at the corner of the handle 12, at the connection region 42, 44 of the respective vertical arm 18, 20 and horizontal bridge first and second ends 22, 24. Each second grip portion radius matches the corner radius of handle 12, such that the outer surface 126, 134 of the respective second grip portion is flush with the outer surfaces of the respective vertical arm 30, 32 and horizontal bridge outer surface 46.

Providing grip portions at the "four corners" of a filing tool, with outer surfaces matching the outer surface contours of the filing tool handle, provides improved grip when fingers are positioned across the diagonal, and provide easier shifting of the user's grip between points along the entire span of the vertical arms—an important consideration in the confined space of a patient's mouth. The convex end-to-end grip profiles 136, 138 and the concave front-to-back grip profiles 172, 174, 176, 178 provide enhanced gripping for any orientation of the gripping fingers.

Figure 7:
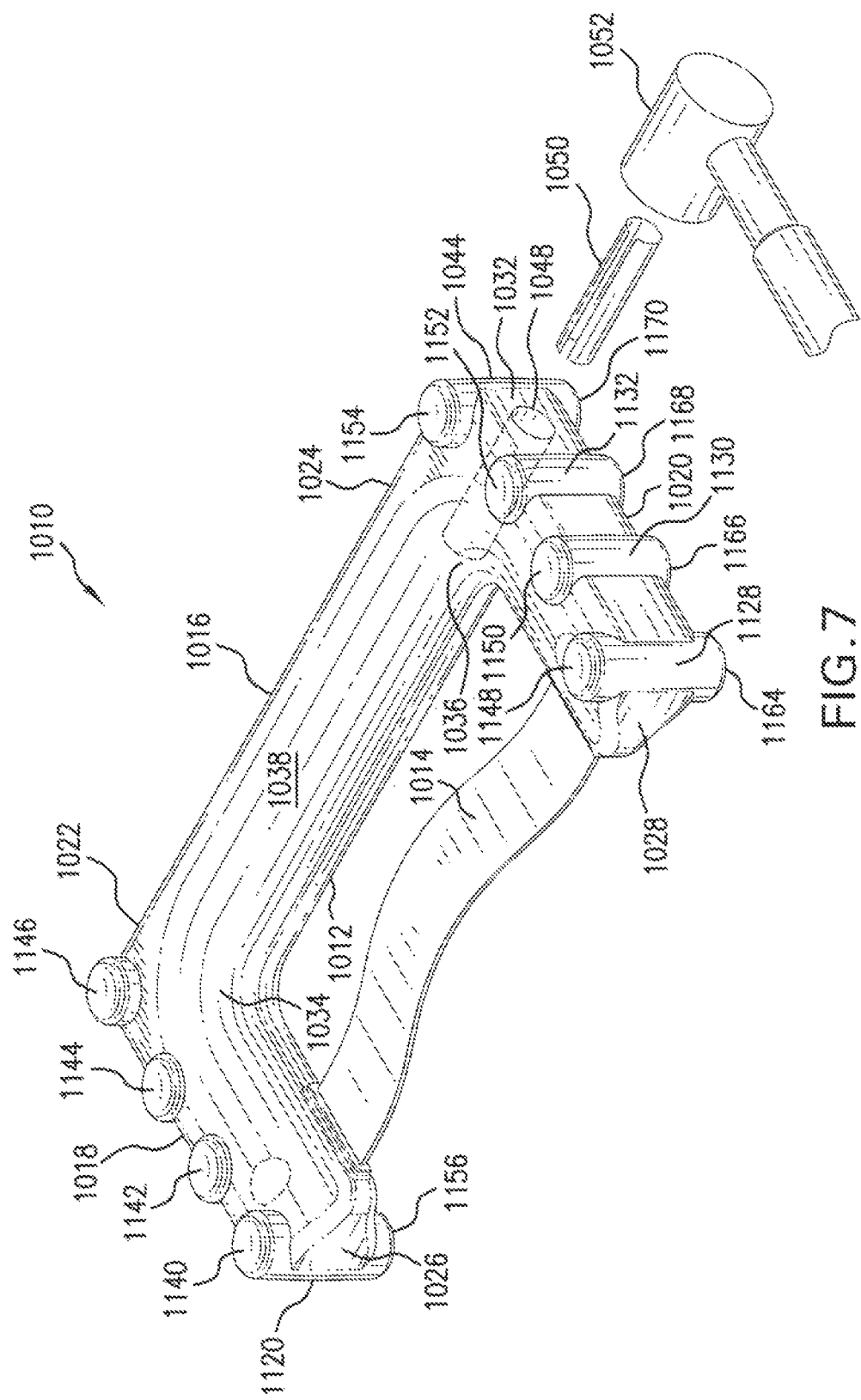
FIG. 7 shows an exploded perspective view of a second embodiment.
Figure 8:
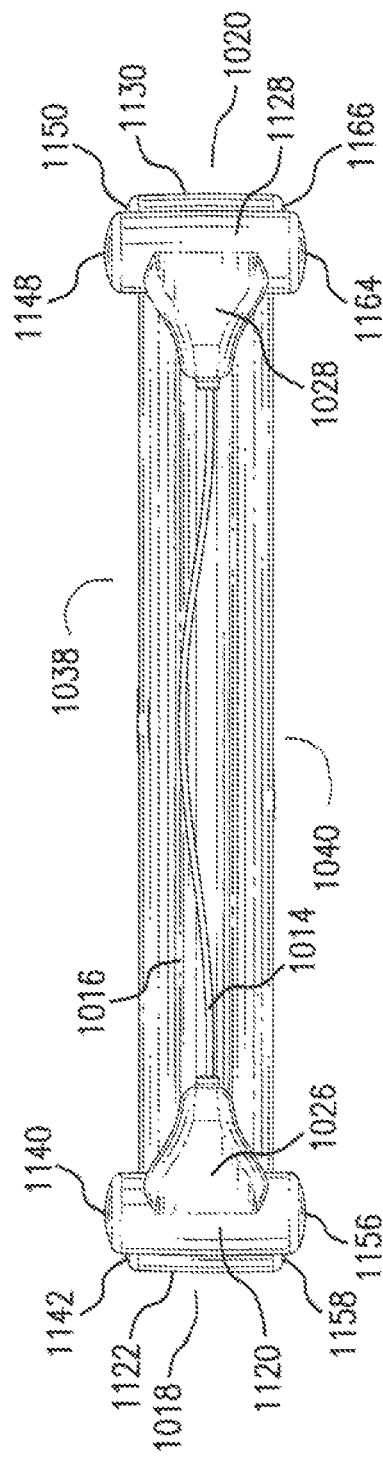
FIG. 8 shows bottom edge view of a second embodiment.
Figure 9:
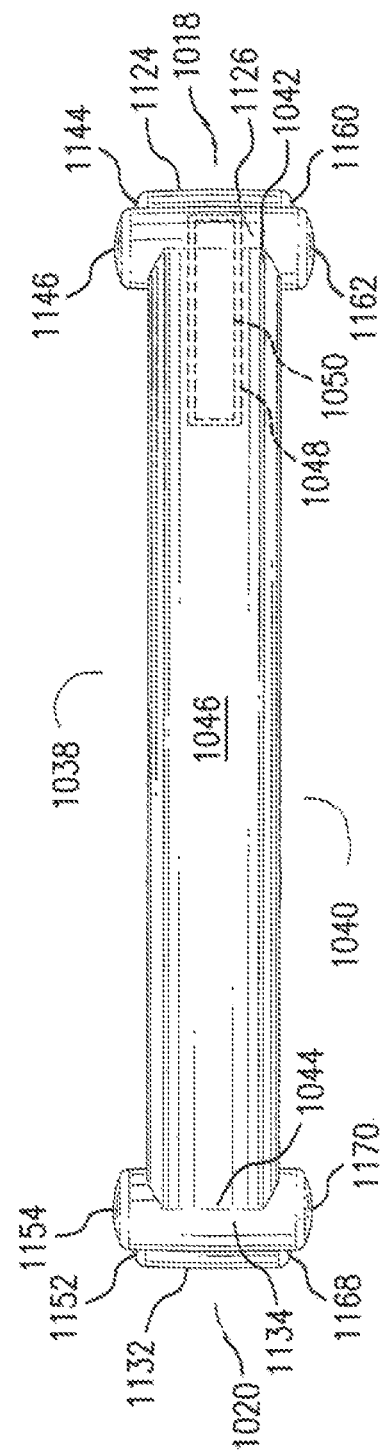
FIG. 9 shows a top edge view of a second embodiment.
Figure 10:
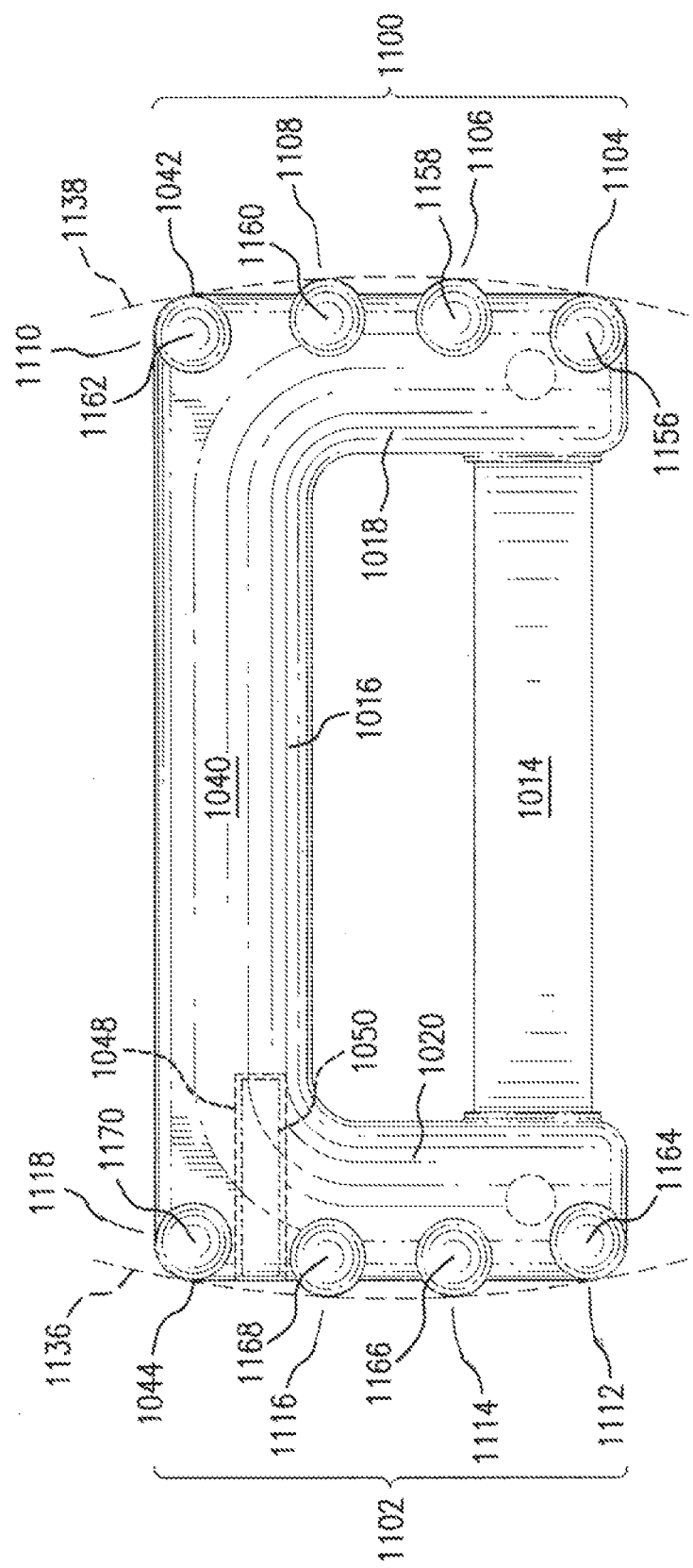
FIG. 10 shows back view of a second embodiment.
Figure 11:
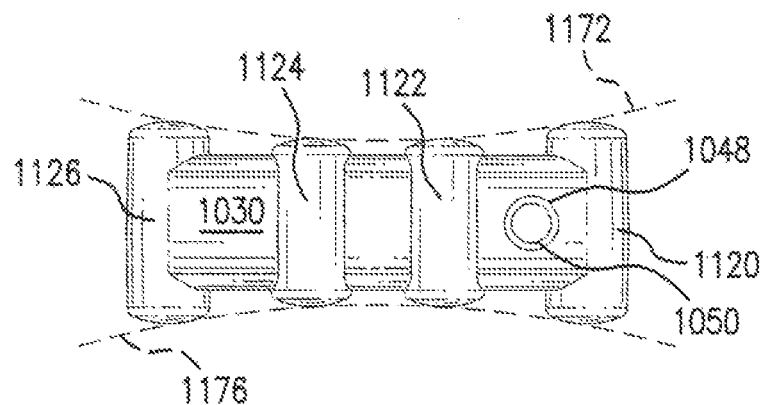
FIG. 11 shows side view of a second embodiment.
Figure 12:
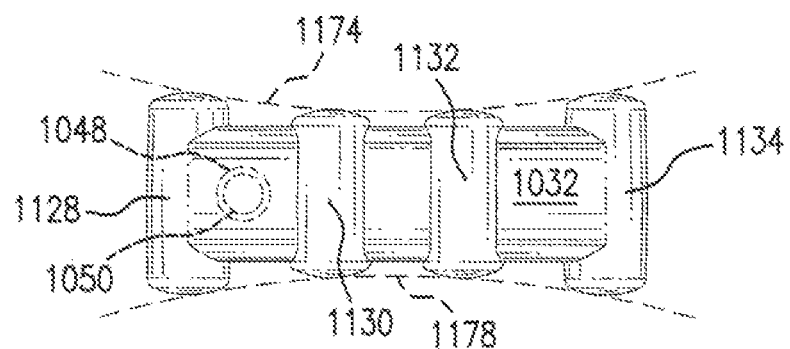
FIG. 12 shows side view of a second embodiment.

Referring to FIGS. 7-12, a second embodiment 1010 is shown demonstrating an improved filing tool couplable to a power-driven dental driver. FIGS. 7-12 generally demonstrate a pre-existing design as in the first embodiment, but the improvement further including a receiving socket 1048 embedded within handle 1012, proximate the second vertical arm—horizontal bridge connection region 1036 and extending into horizontal bridge 1016. Receiving socket 1048 is adapted to receive a coupler 1050, the coupler 1050 to removably couple the apparatus 1010 to a dental driver tool. The pre-existing apparatus includes arcuate handle 1012 and a filing strip 1014. Handle 1012 includes a horizontal bridge 1016 and opposed first and second vertical arms 1018, 1020 extending in parallel from opposite ends 1022, 1024 of the bridge to terminal ends 1026, 1028, the vertical arms 1018, 1020 having outer surfaces 1030, 1032, respectively, and being adapted to hold filing strip 1014 extending between them, the horizontal bridge 1016 and vertical arms 1018, 1020 generally defining a handle plane. Receiving socket 1048 is inset within handle 1012, and adapted to receive a coupler 1050) to removably couple to a dental driver 1052. Receiving socket 1048 does not extend beyond outer surfaces 1120-1134 so as not to interfere with manual gripping. In the embodiment, the edge of receiving socket 1048 is flush with first arm outer surface 1032.

The improvement includes first and second sets 1100, 1102 of partial-cylindrical grip portions 1104, 1106, 1108, 1110 and 1112, 1114, 1116, 1118, respectively, distributed along the outer surfaces 1030, 1032 of the first and second vertical arms 1018, 1020, respectively, the grip portions 1104-1118 extending longitudinally from a first end surface, 1140-154, respectively, proximate to—and extending past—the handle front surface to a second end surface 1156-1170, respectively, proximate to—and extending past—the handle back surface. The partial-cylindrical grip portions 1104-1118 are aligned normal (i.e. with the longitudinal axis aligned transversely) to the handle plane. Grip portions 1104-1118 are described as "partial-cylindrical" because the general shape of the protruding portion of their profiles appears like a cylinder embedded transversely within the respective handle vertical arms 1018 and 1020. Rounded cross-sections such as circles or ovals may provide greater comfort, but a user may prefer sharper edges for use with thicker latex gloves. Rounded cross-sections also make it easier to apply a rounded end surface (1140-1170) if desired, because the three-dimensional shape is less complex. Additionally, rounded shapes may be easier to produce by injection molding methods, with less dimensional instability problems (common at corner profiles) and more uniform melting.

Each set 1100, 1102 includes a first grip portion 1102, 1112 disposed proximate the respective vertical arm terminal end 1026, 1028, a second grip portion 1110, 1118 disposed proximate the connection region 1034, 1036 of the bridge 1016 and respective vertical arm 1018, 1020, and a plurality of spaced-apart interstitial grip portions 1106, 1108 and 1114, 1116 distributed between the first and second grip portions 1104, 1110 and 1112, 1118, respectively.

The outer surfaces 1120, 1122, 1124, 1126 and 1128, 1130, 1132, 1134 of each of the first and second sets 1100, 1102, respectively, trace a convex grip profile, 1136, 1138, respectively. Outer surfaces 1120-1134 refer to the exposed exterior surfaces proximate the first and second arm outer surfaces 1030, 1032, and excluding end surfaces 1140-1170. Convex grip profiles 1136, 1138, can be described as tangent arcs, as each represents a continuous arc intersecting a point on the perimeter our outer surface 1120-1134 of each grip portion 1104-1118.

Each grip portion 1104-1118 extends from a first end surface 1140, 1142, 1144, 1146, 1148 1150, 1152, 1154, respectively, to a second end surface 1156, 1158, 1160, 1162, 1164, 1166, 1168, 1170, respectively. The respective end surfaces 1140-1154 project outward from the respective front and back handle surfaces, 1038 and 1040, to provide enhanced grip when held front-back (in the embodiment, the handle front and back form mirror images). In the embodiment, the end surfaces of each of first and second sets 1100, 1102 of grip portions 1104-1118, project outward from the handle front and back surfaces 1038, 1040, and trace a concave grip profile 1172, 1174, 1176, 1178, with each of the first and second grip portions 1104, 1112 and 1110, 1116, respectively, projecting farther than the respective interstitial grip portions 1106, 1108 and 1114, 1116. In the embodiment, the concave grip profiles 1172-1178 trace a tangent arc which intersects with the end-point of each end surface 1140-1146, 1148-1154, 1156-1162 and 1164-1170, respectively.

In the embodiment, each of the grip portion first and second end surfaces 1140-1170 are rounded, in this case semispherical. Other end surface profiles could be used as well. The rounded surfaces provide greater comfort when tightly gripped.

In the embodiment, each first grip portion 1104, 1112 is located at the vertical arm terminal end 1024, 1026, respectively. Each first grip portion 1104, 1112 radius matches the corner radius of its respective vertical arm terminal end, 1024, 1026 such that each outer surface 1120, 1128 of the respective first grip portion 1104, 1112 is flush with the outer surface of the vertical arm terminal end 1026, 1028, respectively.

In the embodiment, each of the second grip portions, 1110 and 1118, respectively, is located at the corner of the handle 1012, at the connection region 1042, 1044 of the respective vertical arm 1018, 1020 and horizontal bridge first and second ends 1022, 1024. Each second grip portion radius matches the corner radius of handle 1012, such that the outer surface 1126, 1134 of the respective second grip portion is flush with the outer surfaces of the respective vertical arm 1030, 1032 and horizontal bridge outer surface 1046.

The operation of the embodiments is straight forward. The user grips the filing tool handle 12, 1012 with two fingers—typically a thumb and forefinger—at the desired orientation to reach the location to be worked on within a patient's mouth, shifting the orientation of the grip as desired. Any number of methods may be used to produce the improved handle, the most common being by injection molding plastic. However, the handle grip may be accomplished by laser cutting methods, stamping and die cutting, or any other suitable method depending on the handle material.

Figure 13:
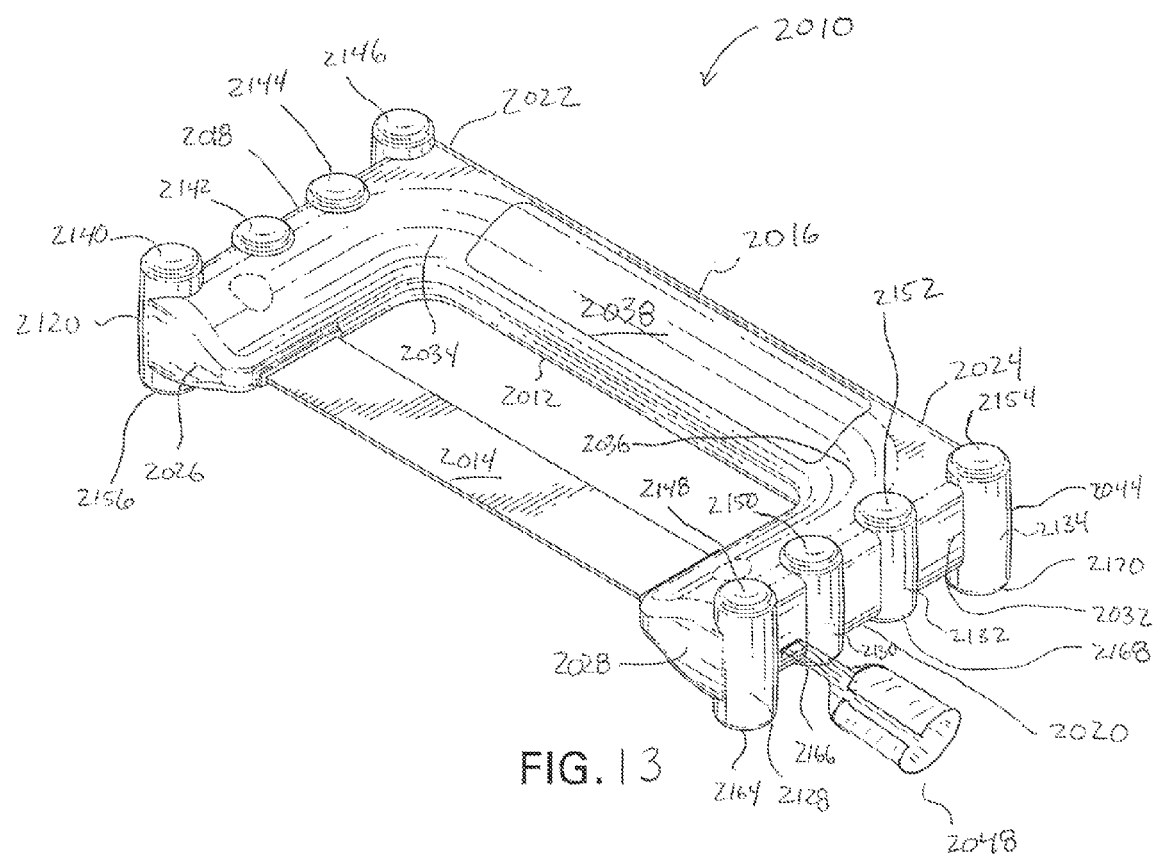
FIG. 13 shows a perspective view of a third embodiment.
Figure 14:
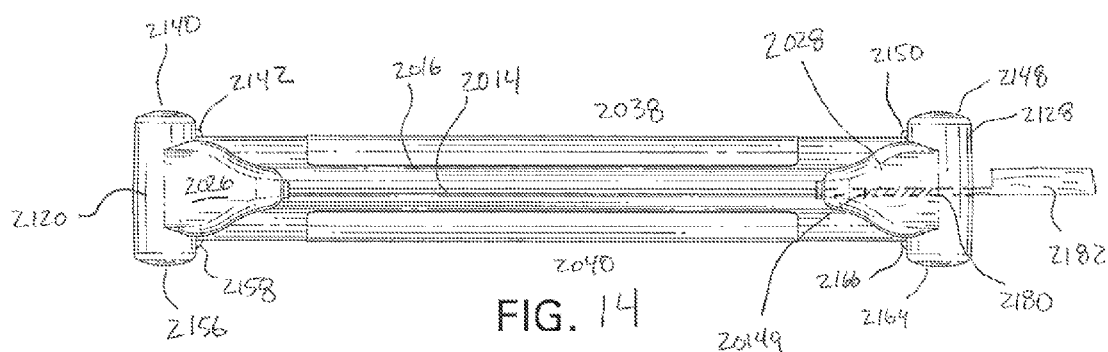
FIG. 14 shows bottom edge view of a third embodiment.
Figure 15:
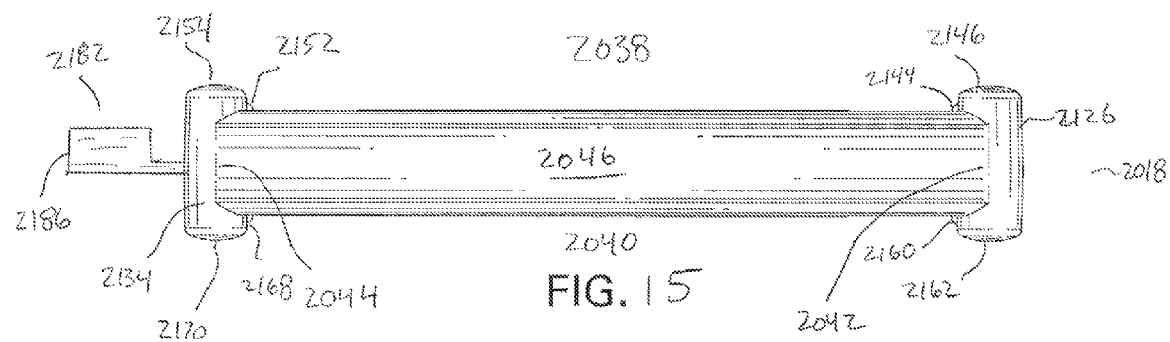
FIG. 15 shows a top edge view of a third embodiment.
Figure 16:
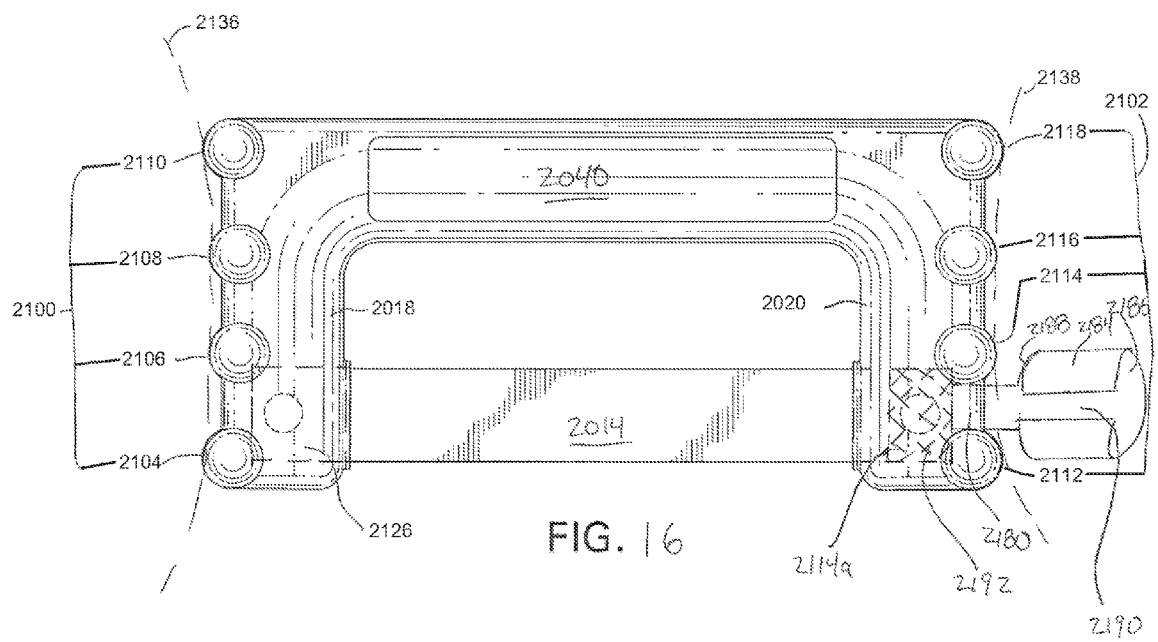
FIG. 16 shows back view of a third embodiment.
Figure 17:
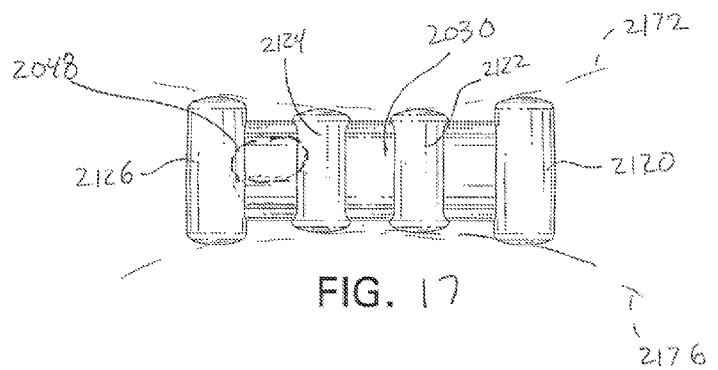
FIG. 17 shows side view of a third embodiment.
Figure 18:
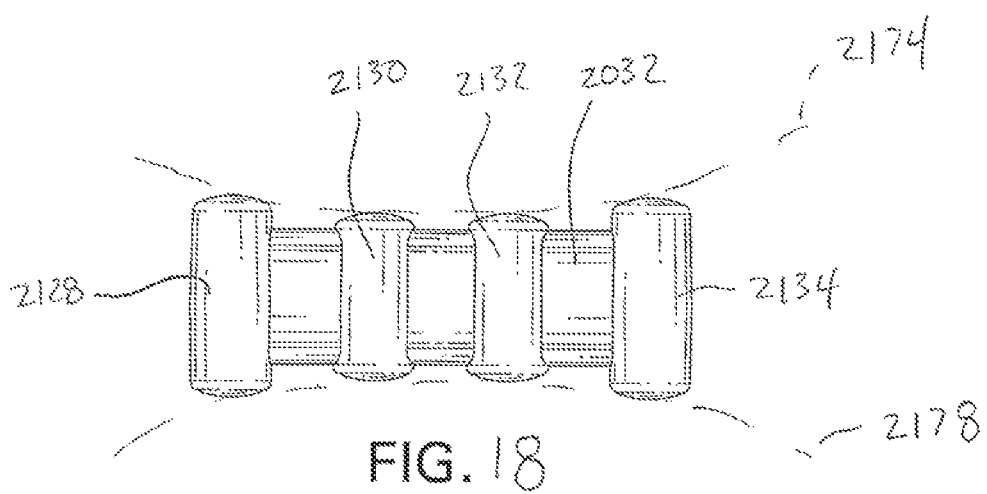
FIG. 18 shows side view of a third embodiment.

Referring to FIGS. 13-18, a third embodiment 2010 is shown demonstrating an improved filing tool couplable to a power-driven dental driver. FIGS. 13-18 generally demonstrate a pre-existing design as in the first and second embodiments, but the improvement further includes a projecting coupler 2048 projecting from handle 2012, proximate the second vertical arm terminal end 2028.

The pre-existing apparatus includes arcuate handle 2012 and a filing strip 2014. Handle 2012 includes a horizontal bridge 2016 and opposed first and second vertical arms 2018, 2020 extending in parallel from opposite ends 2022, 2024 of the bridge to terminal ends 2026, 2028, the vertical arms 2018, 2020 having outer surfaces 2030, 2032, respectively, and being adapted to hold filing strip 2014 extending between them, the horizontal bridge 2016 and vertical arms 2018, 2020 generally defining a handle plane.

The improvement includes first and second sets 2100, 2102 of partial-cylindrical grip portions 2104, 2106, 2108, 2110 and 2112, 2114, 2116, 2118, respectively, distributed along the outer surfaces 2030, 2032 of the first and second vertical arms 2018, 2020, respectively, the grip portions 2104-2118 extending longitudinally from a first end surface, 2140-2154, respectively, proximate to—and extending past—the handle front surface to a second end surface 2156-2170, respectively, proximate to—and extending past—the handle back surface. The partial-cylindrical grip portions 2104-2118 are aligned normal (i.e. with the longitudinal axis aligned transversely) to the handle plane. Grip portions 2104-2118 are described as "partial-cylindrical" because the general shape of the protruding portion of their profiles appears like a cylinder embedded transversely within the respective handle vertical arms 2018 and 2020. Rounded cross-sections such as circles or ovals may provide greater comfort, but a user may prefer sharper edges for use with thicker latex gloves. Rounded cross-sections also make it easier to apply a rounded end surface (2140-2170) if desired, because the three-dimensional shape is less complex. Additionally, rounded shapes may be easier to produce by injection molding methods, with less dimensional instability problems (common at corner profiles) and more uniform melting.

Each set 2100, 2102 includes a first grip portion 2102, 2112 disposed proximate the respective vertical arm terminal end 2026, 2028, a second grip portion 2110, 2118 disposed proximate the connection region 2034, 2036 of the bridge 2016 and respective vertical arm 2018, 2020, and a plurality of spaced-apart interstitial grip portions 2106, 2108 and 2114, 2116 distributed between the first and second grip portions 2104, 2110 and 2112, 2118, respectively.

In the embodiment, the outer surfaces 2120, 2122, 2124, 2126 and 2128, 2130, 2132, 2134 of each of the first and second sets 2100, 2102, respectively, trace a concave grip profile, 2136, 2138, respectively. Outer surfaces 2120-2134 refer to the exposed exterior surfaces proximate the first and second arm outer surfaces 2030, 2032, and excluding end surfaces 2140-2170. Convex grip profiles 2136, 2138, can be described as tangent arcs, as each represents a continuous arc intersecting a point on the perimeter our outer surface 2120-2134 of each grip portion 2104-2118.

Each grip portion 2104-2118 extends from a first end surface 2140, 2142, 2144, 2146, 2148, 2150, 2152, 2154, respectively, to a second end surface 2156, 2158, 2160, 2162, 2164, 2166, 2168, 2170, respectively. The respective end surfaces 2140-2154 project outward from the respective front and back handle surfaces, 2038 and 2040, to provide enhanced grip when held front-back (in the embodiment, the handle front and back form mirror images). In the embodiment, the end surfaces of each of first and second sets 2100, 2102 of grip portions 2104-2118, project outward from the handle front and back surfaces 2038, 2040, and trace a concave grip profile 2172, 2174, 2176, 2178, with each of the first and second grip portions 2104, 2112 and 2110, 2116, respectively, projecting further than the respective interstitial grip portions 2106, 2108 and 2114, 2116. In the embodiment, the concave grip profiles 2172-2178 trace a tangent arc which intersects with the end-point of each end surface 2140-2146, 2148-2154, 2156-2162 and 2164-2170, respectively.

In the embodiment, each of the grip portion first and second end surfaces 2140-2170 are rounded, in this case semispherical. Other end surface profiles could be used as well. The rounded surfaces provide greater comfort when tightly gripped.

In the embodiment, each first grip portion 2104, 2112 is located at the vertical arm terminal end 2024, 2026, respectively. In the embodiment, each of the second grip portions, 2110 and 2118, respectively, is located at the corner of the handle 2012, at the connection region 2042, 2044 of the respective vertical arm 2018, 2020 and horizontal bridge first and second ends 2022, 2024.

Projecting coupler 2048 includes a first part 2180 embedded within second vertical arm 2020 proximate second vertical arm terminal end 1028 and overlapping a terminal end of filing strip 2014, and a second part 2182 extending outward from second vertical arm 2020, the second part 2182 including a coupling 2184 to engage a dental driver. Projecting coupler first part 2180 may be embedded at another location within handle 2012 which provides sufficient depth of material to reliably hold and support projecting coupler 2048, for example proximate second vertical arm-horizontal bridge connection region 1036. Aligning projecting coupler 2048 with filing strip 2014 provides several additional advantages, such as: (1) projecting coupler 2048 interferes less with manual use of the improved file when gripped end-to-end; (2) the force applied by the dental driver is aligned with the resistance from the dental strip, thereby minimizing torque and fatigue on the coupler; and, (3) the filing strip 2014 and projecting coupler 2048 may be formed from a single piece of material, or joined to form a continuous body, to enhance the strength of the coupler and apparatus overall. In the described embodiment, hatched region 2192 shows the overlapping of the projecting coupler first end 2180 and an end of filing strip 2014*a*.

In the third embodiment, the coupler second part 2182 includes a hollow tube coupling 2184 extending from a first end 2186 connected to the projecting coupler first part 2180 to a second end 2188, the tube coupling open at the second end 2188, the tube further including an open seam 2190 extending from the tube second end 2188 to the tube first end 2186. Seam 2190 allows tube coupling 2184 to flex open slightly in order to tightly grip around a corresponding mounting post or stub, or compress slightly to fit tightly within a corresponding receiving sleeve. The thickness and dimensions of tube coupling 2184 are selected to remain within the elastic range of the material when engaged to a selected dental driver tool coupler, such that the spring tension causes tube coupling 2184 to tightly grip a mounting post of a selected dental driver tool.

The concave end-grip design of the third embodiment may be combined with the flush socket coupling design of the second embodiment, and the convex end-grip design of the first and second embodiments may be combined with the projecting coupler design of the third embodiment.

Partial-cylinder portions have additional advantages relating to handles with tapered interior edges. The partial-cylinder outer surfaces and end surfaces provide enhanced surface area for gripping an otherwise thin edge-region, with improved gripping ability over simply knurling the surface or a uniform protrusion pattern distributed over the entire surface.

The improved handle may be used with filing strips mounted under tension or bowed. Additionally, the improved handle is useful in conjunction with a manual filing tool couplable to a power driven dental driver. The partial-cylindrical grip portions extend outward past the coupler used to connect to the driver, providing greater comfort and more reliable manual grip.

Those skilled in the art will recognize that numerous modifications and changes may be made to the preferred embodiment without departing from the scope of the claimed invention. It will, of course, be understood that modifications of the invention, in its various aspects, will be apparent to those skilled in the art, some being apparent only after study, others being matters of routine mechanical, chemical and electronic design. No single feature, function or property of the preferred embodiment is essential. Other embodiments are possible, their specific designs depending upon the particular application. As such, the scope of the invention should not be limited by the particular embodiments herein described but should be defined only by the appended claims and equivalents thereof.

I claim:

1. An improved handle for a dental filing tool, the tool having an arcuate handle with a horizontal bridge and opposed first and second vertical arms extending from opposite ends of the bridge to terminal ends, the vertical arms and bridge having outer surfaces and being adapted to hold a filing strip extending between them, the horizontal bridge and vertical arms generally defining a handle plane and having a front surface and a back surface, the improvement comprising:

first and second sets of partial-cylindrical grip portions distributed along the outer surfaces of the first and second vertical arms, respectively, each of the grip portions extending longitudinally from a first end surface projected outward from the handle front surface to a second end surface projected outward from the handle back surface, each of the grip portions aligned longitudinally normal to the handle plane;

each set comprising a first grip portion disposed proximate the vertical arm terminal end, a second grip portion disposed proximate the connection region of the bridge and respective vertical arm, and a plurality of spaced-apart interstitial grip portions distributed between the first and second grip portions; and, a projecting coupler having a first part embedded within the handle first arm and a second part extending outward from the handle first arm, the second part comprising a dental driver coupling.

2. The improved dental filing tool of claim 1, the improvement further comprising:

wherein, the outer surfaces of each of the first and second sets trace a convex grip profile.

3. The improved dental filing tool of claim 1, the improvement further comprising:

wherein the respective first end surfaces and second end surfaces of each of the first and second sets trace a concave grip profile.

4. The improved dental filing tool of claim 2, the improvement further comprising:

wherein the respective first end surfaces and second end surfaces of each of the first and second sets trace a concave grip profile.

5. The improved dental filing tool of claims 1, 2, 3 or 4, the improvement further comprising:

wherein each second grip portion of the first and second sets is includes a round cross-section and is disposed proximate the corner defined by the intersection of the horizontal bridge outer surface and the respective first or second arm outer surface, and each second grip portion radius matches the respective corner radius such that the outer surface of each second grip portion is flush with the outer surfaces of the respective corner, vertical arm and horizontal bridge.

6. Claim 5, the improvement further comprising:

wherein each first grip portion includes a round cross-section and is disposed at the terminal end of its respective vertical arm, wherein the outer surface of the respective arm defines a corner at its terminal end, and each first grip portion radius matches the corner radius of the respective vertical arm outer surface terminal end corner, such that the outer surface of the first grip portion is flush with the outer surfaces of the vertical arm terminal end corner.

7. The improved dental filing tool of claims 1, 2. 3 or 4, the improvement further comprising:

the coupler second part including a hollow tube extending from a first end connected to the projecting coupler first part to a second end, the tube open at the second end, the tube further including an open seam extending from the second end to the first end.

8. The improved dental filing tool of claim 7, the improvement further comprising:

wherein each of the end surfaces is semispherical.

9. An improved handle for a dental filing tool, the tool having an arcuate handle with a horizontal bridge and opposed first and second vertical arms extending from opposite ends of the bridge to terminal ends, the vertical arms and bridge having outer surfaces and being adapted to hold a filing strip extending between them, the horizontal bridge and vertical arms generally defining a handle plane and having a front surface and a back surface, the improvement comprising:

first and second sets of partial-cylindrical grip portions distributed along the outer surfaces of the first and second vertical arms, respectively, each of the grip portions extending longitudinally from a first end surface projected outward from the handle front surface to a second end surface projected outward from the handle back surface, each of the grip portions aligned longitudinally normal to the handle plane; and, each set comprising a first grip portion disposed proximate the vertical arm terminal end, a second grip portion disposed proximate the connection region of the bridge and respective vertical arm, and a plurality of spaced-apart interstitial grip portions distributed between the first and second grip portions.

wherein, the outer surfaces of each of the first and second sets trace a concave grip profile.

10. The improved dental filing tool of claim 9, the improvement further comprising:

wherein the respective first end surfaces and second end surfaces of each of the first and second sets trace a concave grip profile.

11. The improved dental filing tool of claims 9 or 10, the improvement further comprising:

a receiving socket embedded within the handle first or second arm, the receiving socket adapted to receive a male coupler to removably couple the filing tool to a dental driver, the socket flush not extending beyond the respective set of grip portion outer surfaces.

12. The improved dental filing tool of claim 11, the improvement further comprising:
wherein each second grip portion of the first and second sets is includes a round cross-section and is disposed proximate the corner defined by the intersection of the horizontal bridge outer surface and the respective first or second arm outer surface, and each second grip portion radius matches the respective corner radius such that the outer surface of each second grip portion is flush with the outer surfaces of the respective corner, vertical arm and horizontal bridge.

13. The improved dental filing tool of claim 12, the improvement further comprising:
wherein each first grip portion includes a round cross-section and is disposed at the terminal end of its respective vertical arm, wherein the outer surface of the respective arm defines a corner at its terminal end, and each first grip portion radius matches the corner radius of the respective vertical arm outer surface terminal end corner, such that the outer surface of the first grip portion is flush with the outer surfaces of the vertical arm terminal end corner.

14. The improved dental filing tool of claim 11, the improvement further comprising:
wherein each of the end surfaces is semispherical.

15. The improved dental filing tool of claims 9 or 10, the improvement further comprising:
a projecting coupler having a first part embedded within the handle first arm and a second part extending outward from the handle first arm, the second part comprising a dental driver coupling.

16. The improved dental filing tool of claim 15, the improvement further comprising:
the coupler second part including a hollow tube extending from a first end connected to the projecting coupler first part to a second end, the tube open at the second end, the tube further including an open seam extending from the second end to the first end.

17. The improved dental filing tool of claim 16, the improvement further comprising:
wherein each of the end surfaces is semispherical.

18. The improved dental filing tool of claim 16, further comprising:
wherein the projecting coupler first part overlaps with a terminal end of the filing strip.

19. The improved dental filing tool of claim 16, further comprising:
wherein the projecting coupler first part is connected with a terminal end of the filing strip.

20. The improved dental filing tool of claim 16, the improvement further comprising:
wherein each second grip portion of the first and second sets is includes a round cross-section and is disposed proximate the corner defined by the intersection of the horizontal bridge outer surface and the respective first or second arm outer surface, and each second grip portion radius matches the respective corner radius such that the outer surface of each second grip portion is flush with the outer surfaces of the respective corner, vertical arm and horizontal bridge.

21. The improved dental filing tool of claim 20, the improvement further comprising:
wherein each first grip portion includes a round cross-section and is disposed at the terminal end of its respective vertical arm, wherein the outer surface of the respective arm defines a corner at its terminal end, and each first grip portion radius matches the corner radius of the respective vertical arm outer surface terminal end corner, such that the outer surface of the first grip portion is flush with the outer surfaces of the vertical arm terminal end corner.

22. The improved dental filing tool of claim 15 the improvement further comprising:
wherein each of the end surfaces is semispherical.

23. The improved dental filing tool of claim 15, further comprising:
wherein the projecting coupler first part overlaps with a terminal end of the filing strip.

24. The improved dental filing toot of claim 15, further comprising:
wherein the projecting coupler first part is connected with a terminal end of the filing strip.

25. The improved dental filing tool of claim 15, the improvement further comprising:
wherein each second grip portion of the first and second sets is includes a round cross-section and is disposed proximate the corner defined by the intersection of the horizontal bridge outer surface and the respective first or second arm outer surface, and each second grip portion radius matches the respective corner radius such that the outer surface of each second grip portion is flush with the outer surfaces of the respective corner, vertical arm and horizontal bridge.

26. The improved dental filing tool of claim 25, the improvement further comprising:
wherein each first grip portion includes a round cross-section and is disposed at the terminal end of its respective vertical arm, wherein the outer surface of the respective arm defines a corner at its terminal end, and each first grip portion radius matches the corner radius of the respective vertical arm outer surface terminal end corner, such that the outer surface of the first grip portion is flush with the outer surfaces of the vertical arm terminal end corner.

27. The improved dental filing tool of claims 9 or 10, the improvement further comprising:
wherein each of the end surfaces is semispherical.

28. The improved dental filing tool of claims 9 or 10, the improvement further comprising:
wherein each second grip portion of the first and second sets is includes a round cross-section and is disposed proximate the corner defined by the intersection of the horizontal bridge outer surface and the respective first or second arm outer surface, and each second grip portion radius matches the respective corner radius such that the outer surface of each second grip portion is flush with the outer surfaces of the respective corner, vertical arm and horizontal bridge.

29. The improved dental filing tool of claim 28, the improvement further comprising:
wherein each first grip portion includes a round cross-section and is disposed at the terminal end of its respective vertical arm, wherein the outer surface of the respective arm defines a corner at its terminal end, and each first grip portion radius matches the corner radius of the respective vertical arm outer surface terminal end corner, such that the outer surface of the first grip portion is flush with the outer surfaces of the vertical arm terminal end corner.

30. An improved handle for a dental filing tool, the tool having an arcuate handle with a horizontal bridge and opposed first and second vertical arms extending from opposite ends of the bridge to terminal ends, the vertical arms and bridge having outer surfaces and being adapted to hold a filing strip extending between them, the horizontal bridge and vertical arms generally defining a handle plane and having a front surface and a back surface, the improvement comprising:

first and second sets of partial-cylindrical grip portions distributed along the outer surfaces of the first and second vertical arms, respectively, each of the grip portions extending longitudinally from a first end surface projected outward from the handle front surface to a second end surface projected outward from the handle back surface, each of the grip portions aligned longitudinally normal to the handle plane;

each set comprising a first grip portion disposed proximate the vertical arm terminal end, a second grip portion disposed proximate the connection region of the bridge and respective vertical arm, and a plurality of spaced-apart interstitial grip portions distributed between the first and second grip portions; and, a receiving socket embedded within the handle first or second arm, the receiving socket adapted to receive a male coupler to removably couple the filing tool to a dental driver, the socket flush not extending beyond the respective set of grip portion outer surfaces, wherein, the outer surfaces of each of the first and second sets trace a convex grip profile;

wherein the respective first end surfaces and second end surfaces of each of the first and second sets trace a concave grip profile; and, wherein each of the end surfaces is semispherical.

\* \* \* \* \*